United States Patent [19]

Sabee

[11] Patent Number: 4,813,946
[45] Date of Patent: Mar. 21, 1989

[54] METHOD AND APPARATUS FOR FORMING AND TRANSPORTING ELASTIC RIBBONS

[76] Inventor: Reinhardt N. Sabee, 728 S. Summit St., Appleton, Wis. 54911

[21] Appl. No.: 790,955

[22] Filed: Oct. 24, 1985

[51] Int. Cl.$^4$ .......................... A61F 13/16; B32J 31/00
[52] U.S. Cl. .................................... 604/385.2; 156/160
[58] Field of Search ............... 604/385.2, 365, 385.1; 156/160–165, 229

[56] References Cited

U.S. PATENT DOCUMENTS

| | | | |
|---|---|---|---|
| 4,239,578 | 12/1980 | Gore | 156/164 |
| 4,259,220 | 3/1981 | Bunnelle et al. | 525/99 |
| 4,413,623 | 11/1983 | Pieniak | 604/385 |
| 4,417,935 | 11/1983 | Spencer | 604/385.2 |
| 4,543,099 | 9/1985 | Bunnelle et al. | 604/385.2 |
| 4,547,243 | 10/1985 | Brody | 604/385.2 |
| 4,556,596 | 12/1985 | Meuli | 604/385.2 |
| 4,578,133 | 3/1986 | Oshefsky et al. | 156/164 |
| 4,582,550 | 4/1986 | Sigl | 604/385.2 |
| 4,643,728 | 2/1987 | Karami | 604/385.2 |

Primary Examiner—C. Fred Rosenbaum
Assistant Examiner—Sharon Rose
Attorney, Agent, or Firm—Fuller, Puerner & Hohenfeldt

[57] ABSTRACT

A carrier strip or filament of cold drawable material is utilized to transport discrete lengths of elastic ribbon within a manufacturing apparatus. The elastic ribbons are extruded onto the carrier strip or around the filament and adhere thereto. The carrier strip and elastic ribbon are jointly stretched a predetermined amount. The stretched carrier strip and stretched elastic ribbon are bonded to a component of a final product, as, for example, the backing sheet of a disposable diaper, wherein the elastic ribbons are employed to elasticize the leg areas. The carrier strips greatly facilitate machine handling relatively short lengths of stretched elastic ribbons without waste. The carrier strips may be transversely guided along a predetermined path to follow the hourglass contour of the margins of a diaper having form fitting legs.

10 Claims, 6 Drawing Sheets

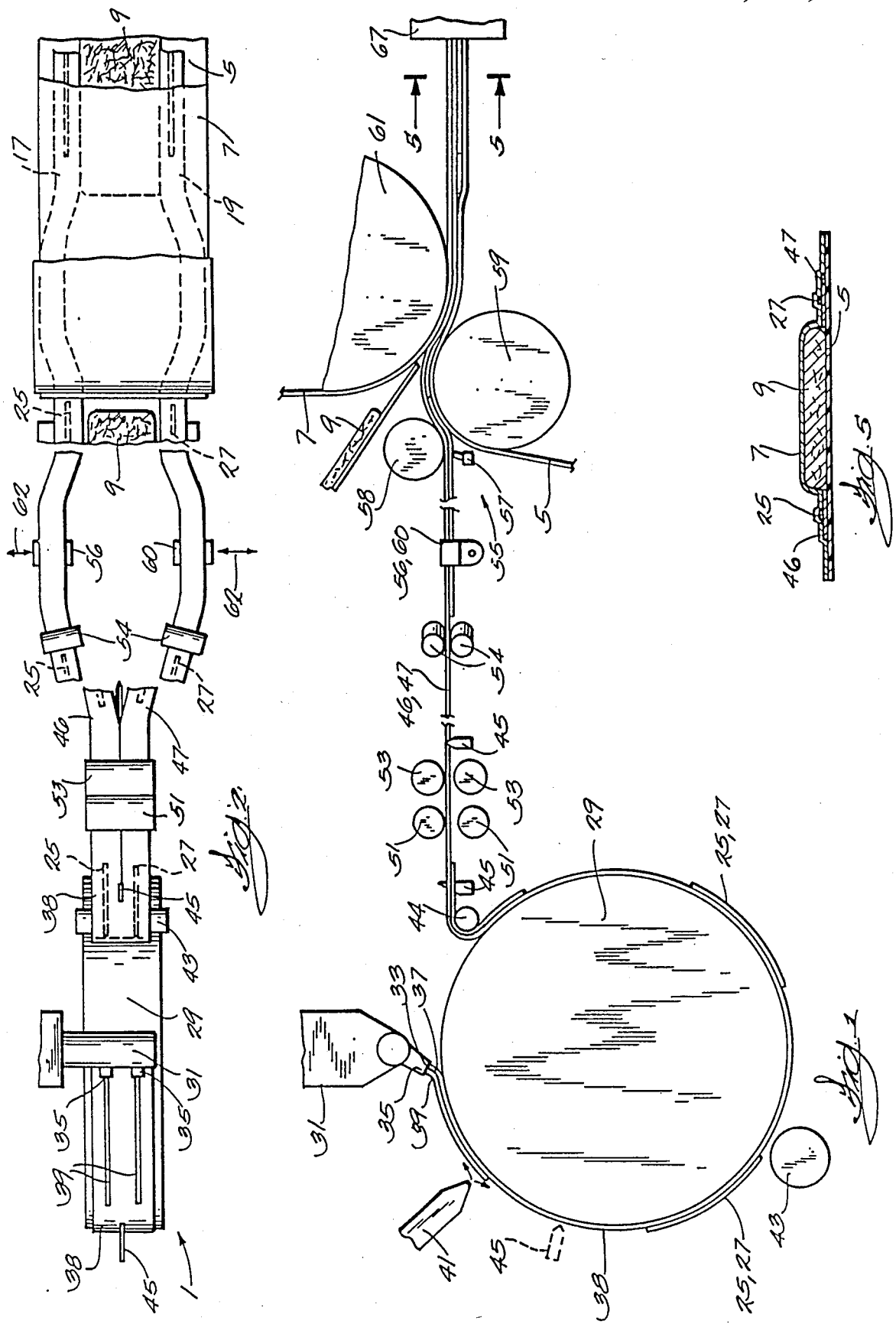

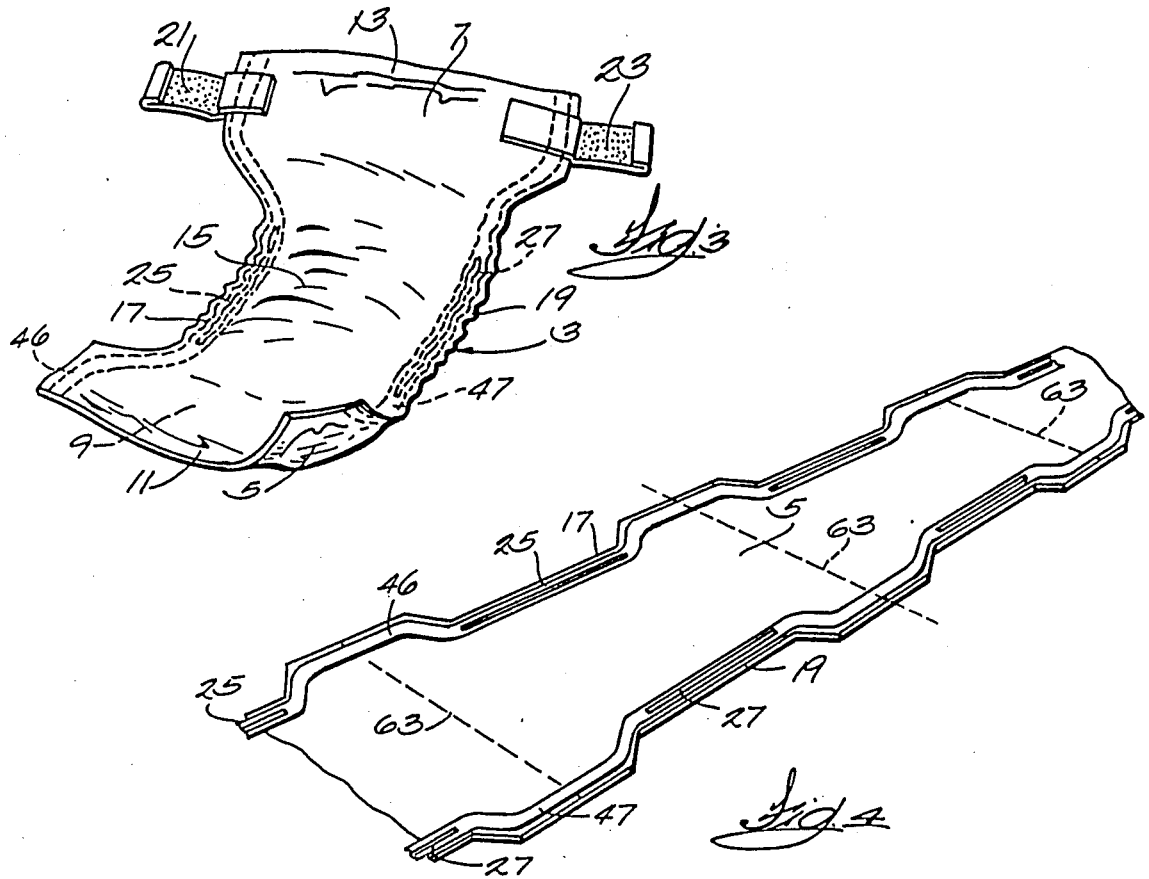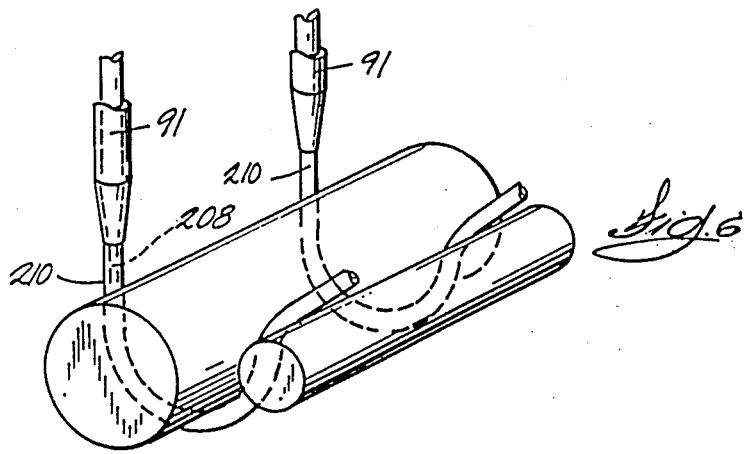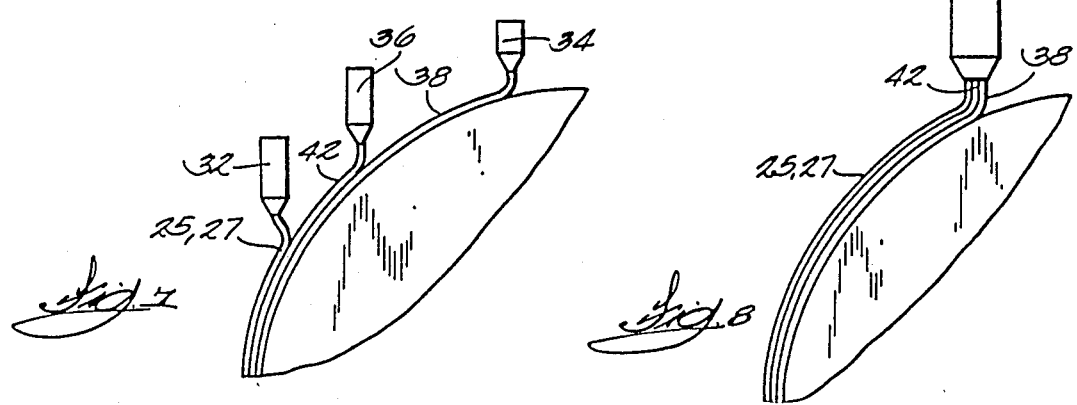

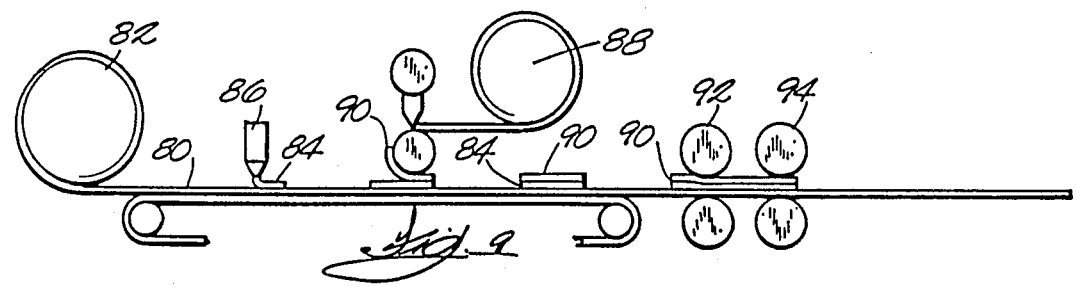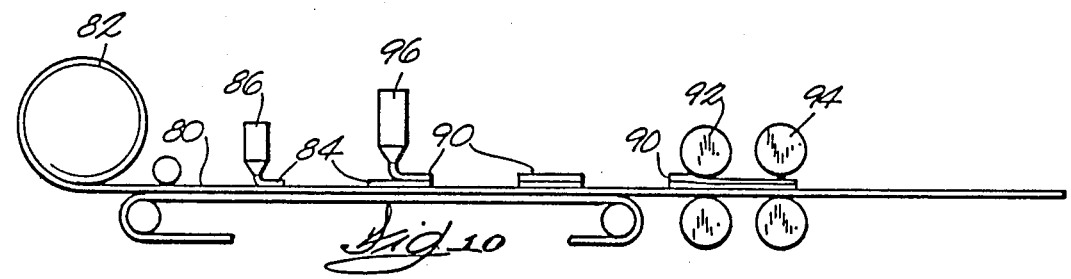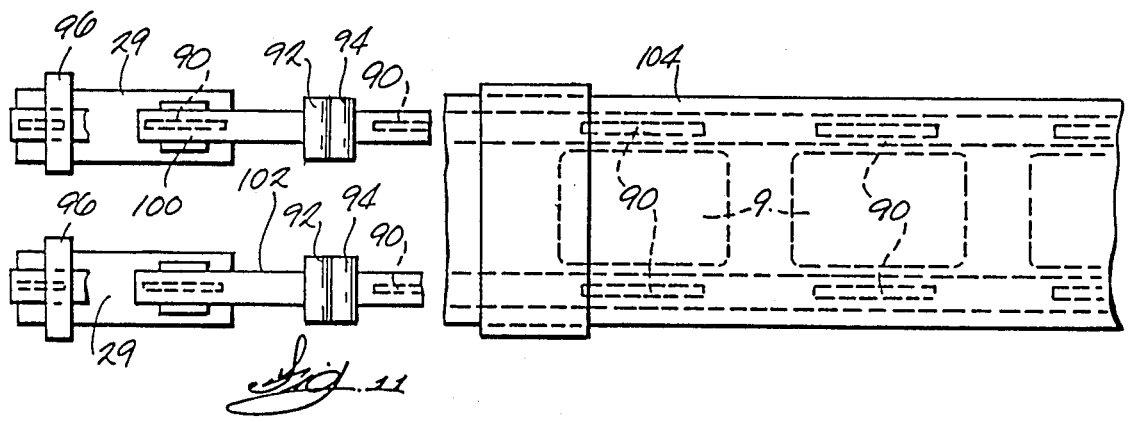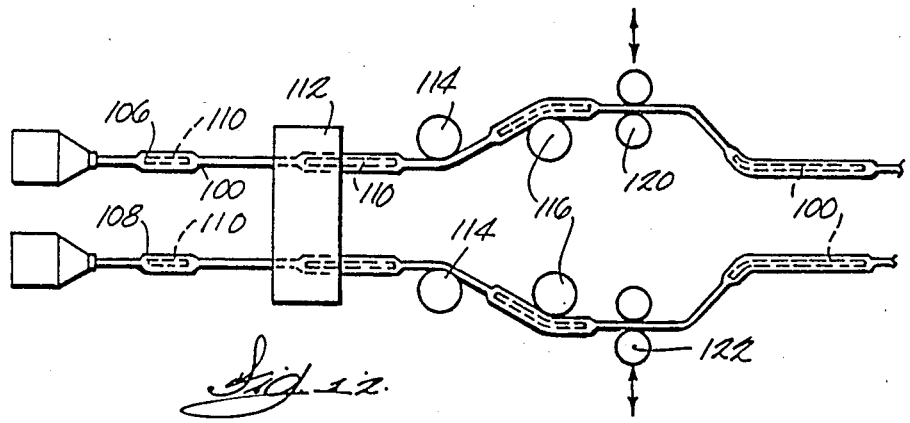

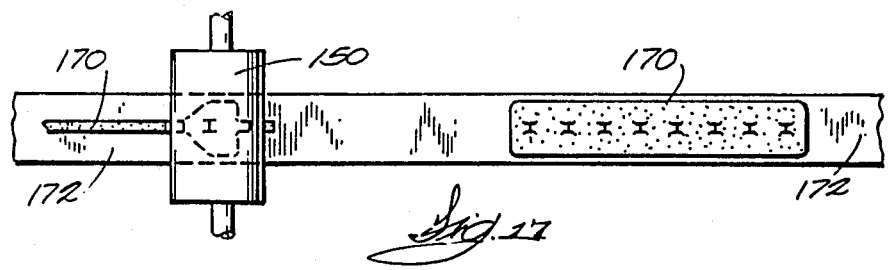
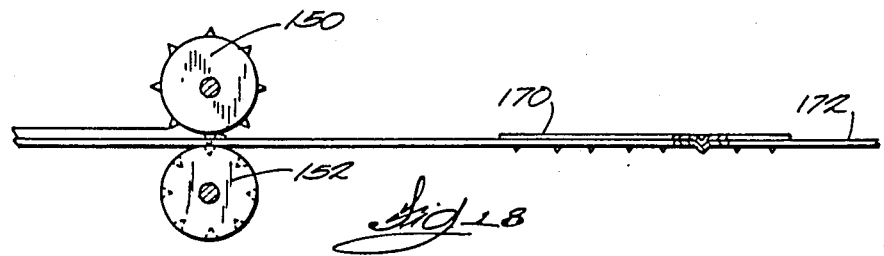
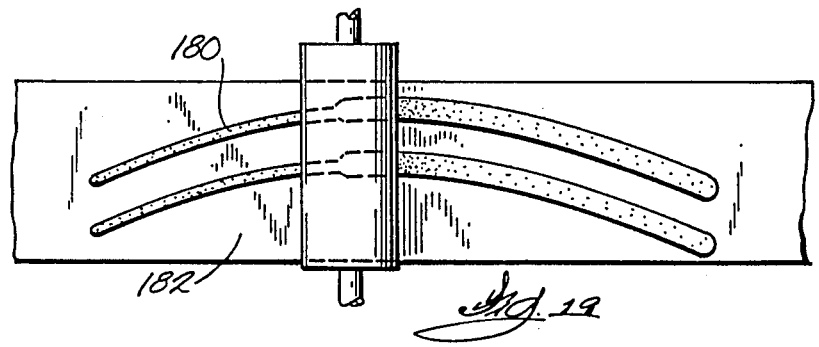
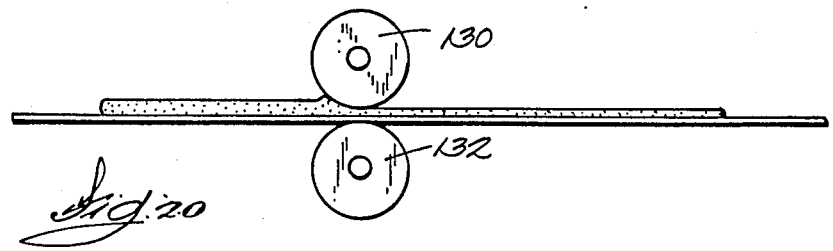

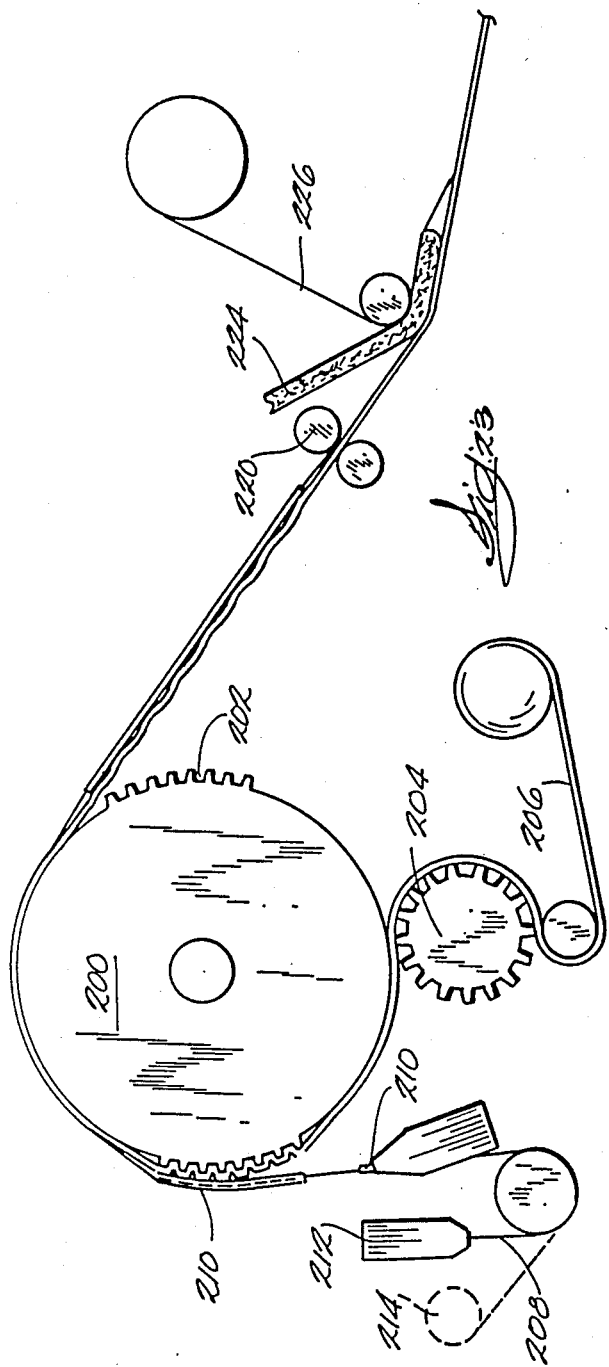

METHOD AND APPARATUS FOR FORMING AND TRANSPORTING ELASTIC RIBBONS

BACKGROUND OF THE INVENTION

1. Field of the Invention

This invention pertains to methods and apparatus for applying elastic ribbons to webs of material, and more particularly to methods and apparatus for applying discrete lengths of stretched elastic ribbon to predetermined areas of a continuously moving web.

2. Description of the Prior Art.

The development of adult and infant disposable diapers is summarized in the article "New Trends in Adult Pads and Infant Diapers," by Francis J. Bouda, Non-Woven Industry, January 1983. Modern disposable diapers employ elastic ribbons, especially in the crotch area, to assist in preventing leakage of body discharges around the wearer's legs.

Various equipment has been developed to deal with the problems associated with handling the elastic ribbons applied to the sheets of diaper material. One problem is the holding of discrete lengths of elastic ribbons in the proper location during the manufacturing operation. The use of vacuum systems to hold the pieces to elastic ribbon is well known and is illustrated in U.S. Pat. Nos. 4,360,398; 4,379,016; and 4,397,704. However, vacuum systems are expensive to build and operate, and they do not provide positive retention of the ribbons.

An associated problem concerns the requirement that the elastic ribbon be applied to the moving web of diaper material such that when the ribbons are relaxed they bunch up the diaper to snug the wearer's legs. One solution to this problem is to corrugate the web material and to apply discrete pieces of elastic ribbon in a relaxed state to the peaks of the corrugations, as disclosed in U.S. Pat. Nos. 4,379,016 and 4,397,704. These designs have the advantage of utilizing only as much ribbon material as is necessary. However, the grooved drums required for corrugating the web are costly to manufacture, as is the vacuum system required to retain the web within the drum corrugations.

A second solution is to attach the elastic ribbons when in the stretched condition to the underlying webs. U.S. Pat. Nos. 4,081,301 and 4,360,398 exemplify this approach. The disadvantage is that a portion of elastic ribbon material is wasted because typically the elastic ribbons are applied only to the crotch regions of the diaper. It has been calculated that 50% of elastic material is wasted by this method. That represents a loss of $75,000.00 per year in some instances. The apparatus of U.S. Pat. No. 4,227,952 applies a stretched elastic ribbon to the web in a manner that does not waste ribbon material, but that apparatus is complicated to manufacture and maintain.

U.S. Pat. No. 3,694,815 utilizes a cryogenic bath in which a stretched elastic ribbon is immersed, thereby immobilizing the ribbon for attaching to the garment fabric; upon warming, elastic ribbon acquires its elastic properties.

U.S. Pat. No. 4,284,454 teaches methods and apparatus for mechanically gripping length of elastic ribbon for transverse placement on a continuous fabrication line. It is evident that the equipment of U.S. Pat. No. 4,284,454 is complicated and costly.

Thus, a need exists for simple and economical apparatus which handles and attaches discrete pieces of elastic ribbon without waste to a continuously moving web.

SUMMARY OF THE INVENTION

In accordance with the present invention, apparatus is provided for forming discrete lengths of elastic ribbon for attachment to an underlying continuously moving web in a more economical and effective manner than was heretofore possible. This is accomplished by supplying a carrier strip or carrier filament and adhering the discrete elastic lengths to the strip. The carrier member affords convenient handling of the elastic during application to the diaper material. The carrier strip can be extruded and the lengths of elastic ribbon bonded to the strip.

The carrier strip can be extruded as a continuous stream, preferably from a cold drawable material onto a rotating chill roll. The elastic ribbons may be extruded in place as a pair of transversely spaced streams of molten or heat softened material which are deposited onto the carrier strip. Alternatively, the elastic ribbon material may be extruded onto the carrier strip a short distance downstream from the carrier strip extruding nozzle. The elastic ribbons are not necessarily extruded continuously onto the carrier strip, but rather they may be extruded intermittently into discrete lengths. A cooling air jet or moisture atomizing means, water cooling and other cooling means may be applied to the extruded carrier strip and elastic ribbon. Upon cooling and solidifying, the molten carrier strip and elastic ribbon extrudates acquire at least some cold drawable and elastomeric properties, respectively, and the elastic ribbons thus formed adhere firmly to the carrier strip. The elastic carrier strip assembly can be formed with co-extrusion nozzles with the carrier extruded in the form of a tube with the elastic extruded within the tube. Adhesive can also be extruded within the carrier tube to secure the elastic ribbon to the carrier. Patterned rollers can be employed rather than or in connection with adhesive to press the elastic into an interlocking pattern with the carrier tube. Patterned rollers can produce elastic bands of various shapes such as shown in FIG. 25.

After the carrier strip or tube and elastic ribbons have cooled sufficiently, they are withdrawn from the chill roll for processing into a finished product, such as a disposable diaper. For that purpose, the carrier strip may be longitudinally slit in half as it continuously moves past a knife, with each half carrying an elastic ribbon.

The carrier strips, being of drawable material, together with the elastic ribbons, are then stretched the proper amount for the product being made. The carrier strips and elastic ribbons are spread apart transversely to the approximate width of the underlying web, thereby locating the elastic ribbons near the web margins.

The elastic ribbons are thus conveniently and inexpensively transported by the carrier strips to an assembly station, where they are combined with the remainder of the diaper components while in a stretched condition, such as an absorbent pad, backing sheet, and facing sheet, into a unitary garment. Upon release of the tension in the stretched elastic ribbons, the ribbons relax to pucker the diaper into a form fitting elasticized garment.

The apparatus of the present invention further includes guide means for guiding the carrier strips and elastic ribbons along predetermined paths. This is necessary to suit the generally hourglass or other outline of a stretched form fitting disposable diaper with cut out portions in the leg areas. The guide means directs the carrier strips and attached elastic ribbons to follow an hourglass outline or other contemplated pattern, thus ensuring that the carrier strip and elastic ribbons track the predetermined path on the longitudinal diaper margins which may be linear or curvilinear. The present invention further includes an elasticized leg disposable diaper that have the drawable carrier strips in its construction. The strips are incorporated along with the absorbent pad, backing sheet, and facing sheet in the diaper. Being readily flexible and of light weight, the carrier strips add neither bulk nor weight to the diaper and they do not affect the diaper performance in any way.

Other objects and advantages of the invention will become apparent from the disclosure.

BRIEF DESCRIPTION OF THE DRAWINGS

FIG. 1 is a schematic side view of the manufacturing apparatus of the present invention;

FIG. 2 is a schematic top view, partially broken, of the apparatus of the present invention;

FIG. 3 is a perspective view of a finished elasticized leg disposable diaper manufactured by the method and apparatus of the present invention;

FIG. 4 is a perspective view of a diaper sheet in the extended flat condition, which occurs only during the diaper manufacturing process and which is manufactured by the method and apparatus of the present invention; and FIG. 5 is a cross-sectional view taken along lines 5—5 of FIG. 1.

FIG. 6 is a diagrammatic view showing co-extrusion of two carrier tubes with internal elastic ribbons.

FIG. 7 is a diagrammatic view showing extrusion of a carrier strip, adhesive and elastic.

FIG. 8 is a diagrammatic view of co-extrusion of a carrier, adhesive and elastic.

FIG. 9 is a diagrammatic view of a modified embodiment in which the carrier strip and elastic are supplied from parent rolls of ribbon.

FIG. 10 is a diagrammatic view of a modified embodiment in which the adhesive and elastic are extruded.

FIG. 11 is a plan view similar to FIG. 2 showing linear application of carrier tubes and elastic ribbon in a linear pattern.

FIG. 12 is a plan view showing application of carrier tubes and elastic in an hour glass pattern.

FIG. 17 is a plan view of a pattern rolled carrier tube with internal elastic ribbon.

FIG. 18 is a side view of the diagram shown in FIG. 17.

FIG. 19 is a plan view of elastic ribbon deposited in non-linear pattern on a carrier strip and squeeze roller.

FIG. 20 is a side view of the diagram in FIG. 19.

FIG. 21 is a diagrammatic view of a modified embodiment of carrier member in the form of an elastic tube with carrier filament inside.

FIG. 22 is a view similar to FIG. 21 of a further modified embodiment.

FIG. 23 is a diagrammatic view of a further modified method of the invention.

FIG. 24 is a top view of a carrier strip and spaced elastic ribbons.

FIG. 25 shows various cross sections of elastic ribbons.

DETAILED DESCRIPTION OF THE INVENTION

Figure 13:
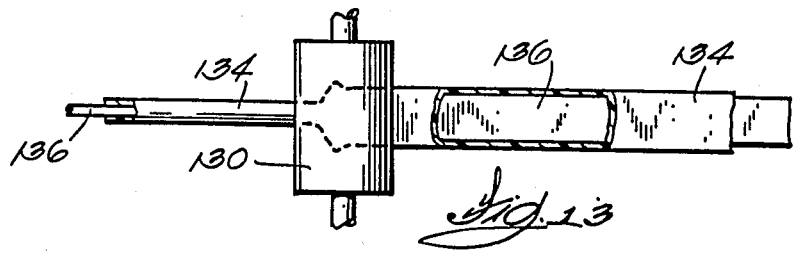
FIG. 13 is a diagrammatic plan view of a carrier strip in the form of a tube with the elastic ribbon inside the tube.

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Referring to FIGS. 1 and 2, manufacturing apparatus 1 is illustrated which includes the present invention. The apparatus finds particular usefulness for manufacturing elastic leg disposable diapers such as is illustrated at 3 in FIG. 3 and is disclosed in U.S. Pat. No. 4,410,324 incorporated herein by reference. However, it will be understood that the invention is not limited to producing products for incontinent applications.

Referring to FIG. 3, the disposable diaper 3 has a backing sheet 5, a facing sheet 7, and absorbent pad 9 interposed between the backing and facing sheets, a front waist area 11, a rear waist area 13, and a crotch area 15 intermediate the two waist areas. Leg areas 17 and 19 are located laterally of the crotch area and intermediate the waist areas. Preferably, the leg areas are indented with respect to the waist areas, so that the stretched diaper has a generally hourglass contour. Waist fastening tapes 21 and 23 may be bonded to the corners of the rear waist area, and they are fastenable to the front waist area when the diaper is fitted to a wearer.

In accordance with the present invention, the manufacturing apparatus 1 (FIGS. 1 and 2) permit the diaper 3 to utilize a pair of transversely spaced elastic ribbons 25 and 27 in an economical and convenient manner. FIG. 1 shows the formation of one elastic ribbon of the pair. The elastic ribbons 25 and 27 are attached to the margins of the diaper in the leg areas 17 and 19, (FIGS. 3, 4) respectively, to elasticize the leg areas and thus provide a snug fit around the legs of the wearer. In FIG. 3, the elastic ribbons 25 and 27 are shown in a relaxed condition in which they cause random pleating or puckering of the back sheet 5, facing sheet 7, and absorbent pad 9.

The manufacturing apparatus in FIG. 1 for supplying the elastic ribbons 25 and 27, FIGS. 1 and 2, includes a chill roll 29 of relatively large diameter and relatively short length. Alternatively, a chilled carrier belt can be employed. For example, the chill roll may be approximately 23 inches in diameter and about 4 inches long. An extruder head 31 having a lower nozzle 33 and a pair of upper nozzles 35 is located above the top point of the chill roll. Alternatively, the extruded carrier strips can be deposited on a flat moving carrier as subsequently described. The extruder head is capable of co-extruding two different materials simultaneously. Alternatively, nozzles 33 and 35 may be contained within separate but adjacent extruder heads 32, 34, as illustrated in FIG. 7.

In the illustrated construction in FIG. 1, the lower nozzle 33 extrudes a thin continuous stream of material 37 across the periphery of the chill roll. The material is preferably drawable when cooled, and the preferable drawable material is polypropylene. The carrier strips are cooled below the polymer softening point. Thus, upon cooling, the stream of material 37 is tranformed into a thin and flexible carrier strip 38. Upper nozzles 35 of extruder head 31 extrude pairs of transversely spaced streams 39 of material that are superimposed upon and adhere to the stream 37 of drawable material. The extruder head 31 includes conventional valves operating under a control system, not illustrated, for controlling nozzle 35. The control system operates in well known fashion to open and close the valves so that the streams 39 from nozzle 35 are extruded intermittently onto the continuous film stream 37. The lengths of the streams 39 are related to the length of the diaper leg areas 17 and 19 (FIGS. 3, 4) as will be explained presently. The elastic ribbons may be extruded with a variable cross section by the use of conventional valves in conjunction with a control system as disclosed in pending U.S. application Ser. No. 530,544 to provide greater tensions in the crotch area than in the waistband region. If adhesives are to be used a third extrusion nozle 36 is added to extruder head 31.

The streams 37 and 39 can be cooled initially by using ambient air or by air from air jets 41. Additional cooling may be provided by one or more secondary chill rolls 43 that contact the streams 39 to flatten and cool them. The streams 39, after cooling and solidifying, acquire elastomeric properties, thereby creating pairs of elastic ribbons 25 and 27 that are firmly bonded to the underlying carrier strip 38. The roller 43 and/or the surface of the drum 29 can be patterned or corrugated to provide an interlocking pattern to secure the elastic to the carrier strip as illustrated in FIG. 18. In FIG. 8 a band of adhesive 42 is extruded unto the carrier strip 38 prior to deposition of the elastic 25, 27. Similarly in FIG. 6 the same procedure is accomplished with a co-extrusion nozzle. The carrier strip can be extruded as a tube 210 with the elastic 208 extruded within the tube by co-extrusion nozzles 91. Alternatively the elastic ribbon can be extruded as a tube enclosing the carrier member filament which can be extruded or fed from a parent roll shown in FIG. 21 and FIG. 22 and FIG. 23. The fialment can be of the same material as a carrier strip and hence is drawable. Securing the elastic to the carrier strip by adhering, bonding, securing, self-adhering, or mechanical bonding are within the purview of the invention and all mean the securement of the elastic to the carrier strip.

The cooled carrier strip 38 with elastic ribbons 25 and 27 bonded thereto pass around roller 44. The carrier strip is then slit longitudinally at about its transverse midpoint into two strips 46 and 47 by a stationary or rotary knife 45. Alternately the carrier may be slit with a hot knife on chill roll 29 or after draw rolls 53 with a stationary or rotary knife, or the carrier-elastic laminate may be slit immediately after deposition on the chill roll while in a heat softened condition with a hot knife as in FIG. 24. In the event carrier tubes are extrudes as in FIG. 6, the knife 45 is not necessary. The carrier strips and elastic ribbons next pass between a pair of pull rolls 51 and a pair of draw rolls 53. The draw rolls 53 rotate at approximately 1⅛ to 3 times the speed of the pull rolls 51. Consequently, the carrier strips and elastic ribbons are stretched to approximately 1⅛ to 3 times their original lengths. The drawable properties of the carrier strips permit the stretching without detrimental effect. The stretching tension is maintained throughout the remainder of the manufacturing process. The two carrier strips are separated transversely from each other, as shown in FIG. 2, by means of two pairs of drive rolls 54.

As shown in FIGS. 3 and 4, the leg areas 17 and 19 of the diaper are cut from the diaper sheet so that the stretched diaper acquires an hourglass contour. To permit the carrier strips to conform to the hourglass contour, the carrier strips 46 and 47 pass between a pair of transversely reciprocating or oscillating guides 56 and 60, respectively. Reciprocating, as used herein, includes oscillating or any form of curvilinear or straight line motions. The guides reciprocate in opposite directions, as indicated by arrows 62. They may be actuated by any suitable mechanism, as, for example, a cam and follower arrangement not illustrated in FIGS. 1 and 2. Consequently, the elastic ribbons are attached near the contoured margins of the finished diaper. The reciprocation of guides 56 and 60 is in timed relationship to the feeding of the absorbent pads 9 at diaper assembly station 55 so that the absorbent pads are located transversely and longitudinally symmetrical with respect to the hourglass contours of elastic ribbons 25 and 27. It will be noted that the length of stretched elastic ribbons approximate the longitudinal length of the leg areas. Thus, the length of the streams of material 39 extruded onto chill roll 39 may be less than the length of the diaper.

At the assembly station 55, the backing sheet 5, which is fed from a parent roll not illustrated in FIGS. 1 and 2, is bonded to the properly guided carrier strips 46 and 47 by adhesive applied to the carrier strips from a pair of applicators 57 located directly under a backing roll 58, FIG. 1. The tension in the carrier strips and elastic ribbons cause the backing sheet to adhere to the carrier strip as the backing sheet and carrier strips pass over roll 59. Subsequently, the absorbent pad 9 and facing sheet 7, which are applied in a conventional fashion from supply stations not shown, are fed to the nip between rollers 59 and 61 where they are bonded in a well known manner to form a continuous web of connected diapers. After the diaper components are assembled, as shown in FIG. 5, the continuously moving web is transported to a first cutting station 67 where the leg areas 17 and 19 are cut from the web as illustrated in U.S. Pat. No. 4,410,324. The web then passes to a second cutting station where it is transversely severed, as along lines 63, FIG. 4. At that time the tension of the elastic ribbons is relaxed, and the individual diapers assume the puckered shape of FIG. 3.

FIG. 9 shows an alternate embodiment of the apparatus and method in which the carrier strip 80 is supplied from a parent roll 82. Adhesive 84 is supplied to the carrier strip 80 by an applicator 86. Elastic ribbon is supplied from a roll 88 and cut into discrete lengths 90. Feed and draw rollers 92, 94 stretch the film 80 and elastic 90.

FIG. 10 shows a modified embodiment in which the elastic ribbon is extruded by an extruder 96.

FIG. 11 is a view similar to FIG. 10 showing two separate carrier strips 100, 102 which can be extruded or taken from two spaced parent rolls 82. The elastic 90 can be supplied by extruders as illustrated in FIG. 10. Draw roller sets 92, 94 draw the elastic carrier strips and stretch the elastic strips 90. The carrier strips 100, 102 are applied to a backing or facing sheet 104 spaced to accomodate deposition of pads 9 which are covered with a top sheet.

FIG. 12 is a plan view showing coextrusion of carrier tubes 106 and 108 of drawable material with elastic cores 110 carried within the tubes. The elastic is intermittently extruded. The composite spaced carrier tubes and elastic are drawn and elastic stretched by pairs of draw rollers at station 112. The drawn tubes are guided by guide rollers 114, 116 and can be deposited on a facing or backing sheet by reciprocating rollers 120, 122 which reciprocate in a transverse direction. Chill rolls can also be employed between the extruders and draw rollers in FIGS. 11 and 12. The chill rolls do not contact the elastic when contained within a carrier tube.

Figure 14:
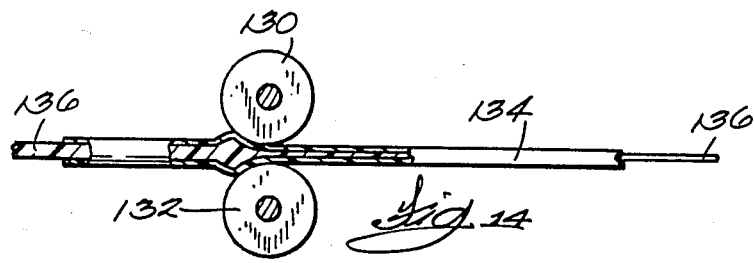
FIG. 14 is a side view of the diagram in FIG. 13.

FIGS. 13 and 14 show application of chill rollers 130, 132 to an extruded carrier tube 134 containing a continuous elastic core 136.

The chill rollers flatten or form the tube into a band strip, or narrow web.

Figure 15:
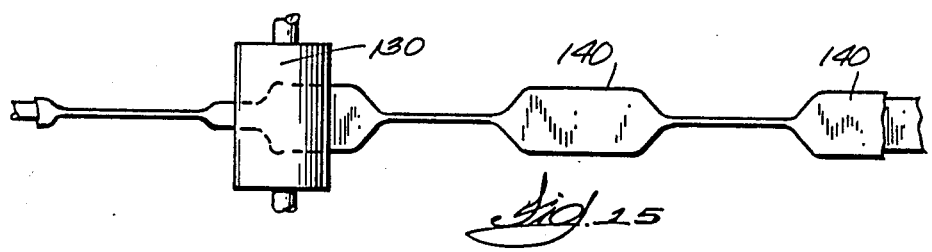
FIG. 15 is a diagrammatic plan view of a carrier strip in the form of a tube with elastic intermittently extruded.
Figure 16:
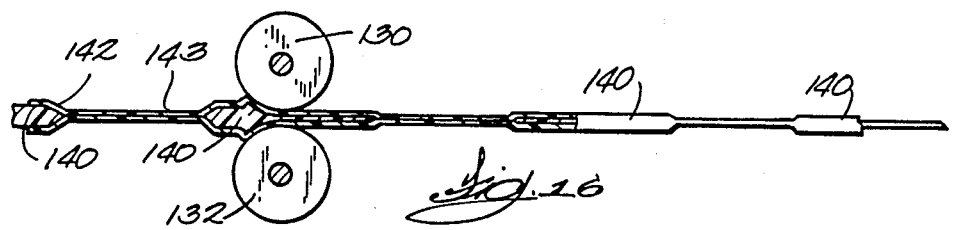
FIG. 16 is a side view of the diagram in FIG. 15.

FIGS. 15 and 16 show the application of chill rolls 130, 132 to an extruded elastic-carrier strip assembly in which the discrete lengths of elastic 140 are intermittently extruded within the carrier tube 142. The elastic lengths are connected by small carrier tube lengths 143. Upon flattening, the carrier strip will have the appearance shown in FIG. 15.

FIGS. 17 and 18 show the use of patterned chill rolls 150 and 152 which mate to form an interlocking pattern of the squeezed and formed elastic ribbon 170 on a carrier strip 172. Adhesive could also be employed to secure the elastic to the carrier strip.

FIGS. 19 and 20 show intermittent deposition of discrete elastic lengths 180 in a pattern on a flat carrier strip 182. The patterned deposition of the elastic can be provided by reciprocating the extruders.

FIG. 23 shows a drum 200 with corrugating teeth 202 which cooperate with corrugating roll 204 to corrugate the backing or facing sheet 206. An assembly of a filament 208 within an elastic tube 210 or spaced tube segments 210 is applied over the corrugated backing. FIGS. 21 and 22 show the filament 208 and tube 210.

The filament 208 can be extruded from an extruder 212 or alternatively supplied from a parent roll 214. The filament is fed through the nozzle of the extruder and the elastic extruded around it.

Draw rolls 220 pull the assembly or lamina from the roll 200 and simultaneously remove the corrugations, draw the carrier filament 208 and stretch the elastic tube 210. The lamina is then assembled with a pad 224 and the other a backing or facing sheet 226 while the elastic remains stretched.

Thus, it is apparent that there has been provided, in accordance with the invention, methods and apparatus for economically and conveniently forming and transporting individual pieces of elastic ribbon that fully satisfy the objects, aims, and advantages set forth above. While the invention has been described with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

The carrier strip and elastic ribbons can be firmly adhered by autogenous bonding if the materials are compatible. If the carrier strip and elastic ribbon are dissimilar materials and not compatible with each other, an adhesive is used for securement. A mechanical bond or a mechanical interlock can be used solely by itself or in conjunctiobn with self bonding, autogenous bonding, or adhesive bonding. The term autogenously bonded as used herein is used to describe the tendency of the two layers to adhere to each other when the surfaces are brought into contact with or without heat or by the application of heat and pressure alone and without any solvent or adhesive application. The terms self adhering, self bonding, autogenous bonding and mechanical bonding (obtained by passing heat softened extrudates between two patterned chill rolls) as used herein are used interchangeably and means the attachment or the securement without the use of solvents or adhesives. The terms secure, attach, bond and adhere as used herein means attachment or securement by any one or any combination of above listed terms and including the use of adhesives and solvents. The term adhesive bonds as used herein means the attachment or bonding with the use of materials having adhesive properties or solvents.

Thermoplastic rubbers suitable for extrusion such as Shell Chemical Company's Kraton 2000 and 3000 Series and GX-2701, DuPont's thermoplastic elastomer, Alcryn, B. F. Goodrich's thermoplastic polyurethanes, Upjohn's thermoplastic polyurethanes, J. Von's thermoplastic elastomers, Stevens thermoplastic film and Mearthane Products polyurethane elastomers are thermoplastic rubbers which can be employed for the elastic bands. These rubbers combine the properties of vulcanized elastomers and the processing of vulcanized elastomers and the processing advantages of thermoplastics. Standard thermoplastic processing equipment can be used to form the rubber processing equipment can be used to form the rubber extrudates. The present invention, however, is not limited to the above listed thermoplastic rubbers, for any elastic thermoplastic material which is soft and flexible will be suitable for the aforementioned elastic bands.

Both natural and synthetic vulcanized rubbers can be secured to the extruded carrier strip and fed into the stretch and draw unit and subsequently to the assembly station, or the carrier strip, as used, may be in a roll form, or the carrier strip and the elastic ribbon may be assembled as a laminate in roll form prior to being unwound into the assembly station.

Although the above mentioned thermoplastic rubbers can be processed in ways similar to those used for conventional thermoplastic polymers, it is very difficult to extrude them into thin films. However, by extruding a thick film of thermoplastic rubber onto a carrier strip and squeezing said molten or fused extrudate between two chill rolls, thin films of any desirable thicknesses are obtained, and can range from less than 0.0001" to 1/16" or more. By using chill rolls with patterns, as herein disclosed, cross-sectional shapes and forms in varying thicknesses can be fabricated in various forms such as tapered, bell shaped or double ribbons connected by a thin web some of which are shown in the drawings.

In the preferred method, the carrier strip is prepared by extruding molten or fused polymer through a slotted or tubular orifice and drawing the polymer away from the orifice at a velocity greater than the velocity of extrusion to effect a substantial draw-down in the molten state prior to solidification, thereby achieving at least partial molecular orientation of long chain molecules as well as a great reduction in cross-sectional area during the hot draw-down while being cooled by the ambient air. The extent to which the molecular orientation is achieved depends on the amount the carrier strip is stretched, which is controlled by the speed with which the polymer is ejected from the die, the speed of withdrawal, and the degree of cooling by the ambient air. To further speed up cooling and setting of the partially drawn carrier strip, secondary air, fluid, or vapor streams may be introduced prior to contact with the chill roll, whereupon the partially hot drawn carrier strip is cooled to a set condition. Alternatively, sufficient chilling of the secondary fluid streams will cool the carrier strip to a set condition without the necessity or need of a chill roll.

Subsequent to the final cooling by the secondary fluid means or by the chill roll means adhesive and fused elastic material are deposited on the cooled carrier strip, which is in direct contact with the chill roll, whereon the elastic strip solidifies to a set condition and becomes elastomeric or stretchable and bonded to the carrier sheet. Following solidification of the elastic ribbon, the two materials are subjected to a cold stretch wherein drawing takes place at a temperature below the polymer melting point, and the elastic ribbon is stretched. This draw is continued until the desired additional amount of molecular orientation has been imparted to the carrier strip. If a co-extrusion die is used the coextruded laminate of carrier sheet, adhesive, and elastic ribbon are cooled simultaneously and subsequently drawn as described above. The total amount of orientation imparted to the carrier strip is determined by the following three requirements.

1. The final thickness of the carrier strip as it enters the assembly station with very thin materials being highly cost efficient. The material thickness may range from 0.0001" to 0.015" preferably 0.00015" to 0.0008."

2. The amount of elongation to be imparted to the elastic by the wearer of the garment, the range being from 10% to 600% elongation to preferably 20% to 300%.

3. The remaining amount of stretch or drawing to be left in the carrier strip to allow efficient machine operation without strip breakage and costly shutdowns. If the polymer used is of sufficient strength the strip may be substantially fully drawn which greatly reduced material costs.

In addition to self bonding, autogenous bonding, and fuse bonding, the elastic ribbons may be secured with adhesives some of which are listed below. They may be applied with applicators, both hot and cold; extruded, and co-extruded whereby they are extruded with one or both of the materials to be bonded to each other. Suitable adhesives are pressure sensitive adhesives, cold adhesives, hot melt adhesives, releasable adhesives, elastomeric hot melt adhesives, and pressure sensitive hot melts. Some of the manufacturers supplying suitable adhesive are as follows: Eastman Chemical Co., Hot Melt Adhesive No. 13375; H. B. Fuller Co., Hot Melt Adhesive No. HM1533; Shell Chemical Co., Kraton; Rohm and Haas Co., Hot Melt Adhesive QR-969; Borden Chemical Co., Casco Melt HA-7981, and Findley Co., Elastomeric Hot Melt Adhesives.

Suitable thermoplastic polymers suitable for use in the instant invention include the following: Polyolefinspolyethylenes, polypropylenes; polyamidesnylons; polyesters; polyurethanes; polyacrylics; polyvinyl acetate; including copolymers of such compounds and mixed polymers of such compounds. Any drawable thermoplastic polymer or at least partially drawable polymer can be used for the carrier strip even though it contains some elastomeric material. As used herein the term "carrier strip∞ and "carrier member" are used interchangeably and both include filaments.

I claim:

1. A disposable diaper comprising a backing sheet, a facing sheet, an absorbent pad located intermediate said backing and facing sheets, strips of drawn, molecularly oriented, substantially non-elastic, permanently elongated, and flexible thermo-plastic material located on opposite sides lateral of said pad and inbetween said facing and backing sheets, and having a width less than the backing and or facing sheets and elastic ribbons having a relaxed length less than the length of the backing or facing sheet or both and said ribbons adhered to said strips,
    so that the drawn and permanently elongated strips constrain the extensibility of the stretched elastic ribbons.

2. The disposable diaper of claim 1 in which the elastic ribbons are adhered to said backing or facing sheets or both.

3. An elastic leg disposable diaper comprising:
    (a) a backing sheet and a facing sheet, each sheet having a front waist area and a rear waist area and a crotch area intermediate the two waist areas, the crotch area having leg areas positioned laterally of the crotch area and intermediate of the waist areas;
    (b) an absorbent pad interposed between the backing and facing sheets in the crotch area;
    (c) spaced, flexible, relatively non-elastic molecularly oriented, and permanently elongated continuous carrier constraining strips of less width than the backing sheet interposed between the backing and facing sheets and adjacent each margin thereof and extending between the waist areas, each carrier strip being molecularly oriented and permanently elongated along a predetermined portion of the length thereof; and
    (d) an elastic ribbon having a relaxed length less than the length of the backing and or facing sheets and said carrier strips attached to each continuous carrier constraining strip in the leg areas,
    so that the elastic ribbons pucker the diaper at least in the crotch area when in the relaxed condition and the continuous carrier constraining strips constrain the extension of the elastic ribbons.

4. The disposable diaper of claim 3 wherein the leg areas are cut from the backing and facing sheets thereby producing generally hourglass contours in the margins thereof to conform to the legs of the wearer, and wherein the carrier strips substantially follow the hourglass contour.

5. An elastic leg disposable diaper of claim 3 in which the elastic ribbons are bonded to said backing and/or facing sheets.

6. The disposable diaper of claim 3 wherein the permanently elongated length of the continuous carrier strip is approximately 1⅛ to 3 times its original length at least in the area of elastic ribbon attachment thereto.

7. The disposable diaper of claim 3 wherein the carrier strips limit the extensible capabilities of the elastic ribbons to approximately 1⅛ to 3 times their relaxed lengths.

8. The disposable diaper of claim 3 wherein the carrier strips constrain the extension of the elastic ribbons to less than 10 times their original lengths.

9. The disposable diaper of claim 3 wherein the carrier strips are molecularly oriented and permanently elongated at least in the areas of elastic ribbon attachment thereto.

10. The disposable diaper of claim 3 wherein the elastic ribbons have predetermined variable cross-sections along their lengths.

* * * * *